United States Patent [19]

Linder

[11] Patent Number: 4,475,555
[45] Date of Patent: Oct. 9, 1984

[54] UNIVERSAL MEASURING ATTACHMENT FOR ESOPHAGEAL STETHOSCOPES

[76] Inventor: Gerald S. Linder, 16693 Charmel La., Pacific Palisades, Calif. 90272

[21] Appl. No.: 154,580

[22] Filed: May 29, 1980

Related U.S. Application Data

[63] Continuation of Ser. No. 949,646, Oct. 10, 1978, abandoned.

[51] Int. Cl.$^3$ .............................................. A61B 5/02
[52] U.S. Cl. .................................. 128/670; 128/736; 128/773
[58] Field of Search ............... 128/773, 736, 725, 642, 128/673, 303.15, 247, 670, 349 R, 348; 604/158-160, 171, 264, 280, 283-284

[56] References Cited

U.S. PATENT DOCUMENTS

| | | | |
|---|---|---|---|
| 2,004,559 | 6/1935 | Wappler et al. | 128/303.15 |
| 3,081,765 | 3/1963 | Kompelien | 128/721 |
| 3,212,207 | 10/1965 | Searing | 174/112 |
| 3,216,420 | 11/1965 | Smith et al. | 128/247 |
| 3,707,972 | 1/1973 | Villari et al. | 128/247 |
| 3,726,269 | 4/1973 | Webster, Jr. | 128/348 X |
| 3,766,916 | 10/1973 | Moorehead et al. | 128/214.4 |
| 3,951,136 | 4/1976 | Wall | 128/736 |
| 4,073,287 | 2/1978 | Bradley et al. | 128/642 |
| 4,096,862 | 6/1978 | De Luca | 128/1.2 |
| 4,181,549 | 1/1980 | McPhee | 156/146 |
| 4,263,921 | 4/1981 | Trugillo | 128/736 |

OTHER PUBLICATIONS

Ellenwood et al.; IBM Technical Disclosure Bulletin; "Central-Body Temperature Apparatus"; vol. 11, No. 11, 4/69.

Primary Examiner—Lee S. Cohen
Assistant Examiner—Angela D. Sykes
Attorney, Agent, or Firm—B. F. Spencer

[57] ABSTRACT

A measuring attachment for use with a variety of sizes of esophageal stethoscopes is disclosed for enabling the measurement of a number of patient body conditions while monitoring a patient's body sounds in the region of the esophagus. The measuring attachment includes a coupling adapter having an input opening for coupling to the open end of an esophageal stethoscope, an output opening for coupling to an acoustically-responsive instrument, and a central bore extending through the coupling adapter between the input and output openings for the passage of the patient's body sounds. A lateral passageway is provided from an outside surface of the coupling adapter and through the adapter for entry into the open end of the stethoscope. The lateral passageway enables a pair of electrically-conductive wires to slidably pass from the outside of the coupling adapter through the adapter to an adjustably-positionable sensing probe. The sensing probe is insertable into the stethoscope and may be adjustably placed at any suitable position therein. A suitable measuring instrument for displaying the measurement is connected to the output terminals of the pair of conductive wires and may be located remotely from the coupling adapter for the convenience of the physician. The esophageal stethoscope may be intubated into the patient with the measuring attachment of the invention in place, or the measuring attachment may be inserted into, or may be removed from, the stethoscope after its intubation.

6 Claims, 8 Drawing Figures

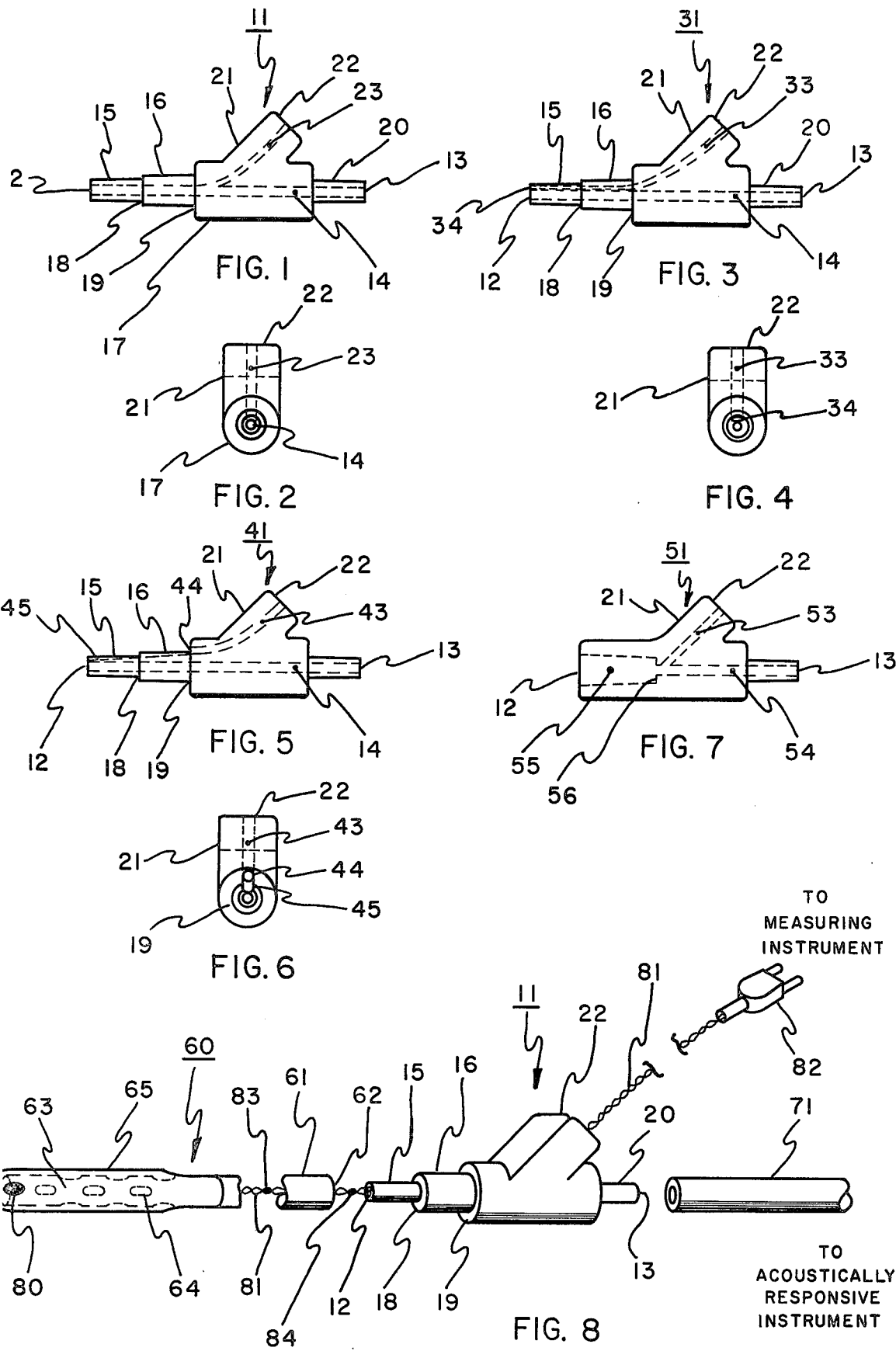

UNIVERSAL MEASURING ATTACHMENT FOR ESOPHAGEAL STETHOSCOPES

This is a continuation of application Ser. No. 949,646 filed Oct. 10, 1978, abandoned July 11, 1980.

BACKGROUND OF THE INVENTION

The present invention relates to esophageal stethoscopes, and, in particular, to a reusable measuring attachment having an adjustably-positionable sensing probe for use with a variety of sizes and types of esophageal stethoscopes.

The conventional esophageal stethoscope consists of a long, transparent, hollow plastic tube open at its proximal end and perforated adjacent its distal end with a group of cylindrically-spaced holes. The distal end of the tube and the group of spaced holes is closed and hermetically sealed by a thin, flexible, cylindrical cuff or sheath surrounding the distal end portion. The open proximal end of certain esophageal stethoscopes is provided with a securely attached plastic connector for acoustically coupling the stethoscope to the flexible rubber tubing of the physician's earpiece.

Esophageal stethoscope are available in different sizes and lengths from 12 French, for use in pediatrics, to 24 French, for large adult patients. Length generally exceeds 50 centimeters. The distal end of the stethoscope is intubated through the patient's mouth, past the oral pharynx and into the esophagus. The stethoscope may be positioned at varying depths to monitor the patient's body sounds at different locations in the esophageal region. The esophageal stethoscope must be discarded after use and cannot be reused.

The temperature of the patient may be measured by an esophageal stethoscope provided with a thermocouple or thermistor situated in the distal end portion and electrically connected to a pair of conductive wires. In one prior art embodiment, a thermocouple is securely attached to the inside wall of the distal end portion, and the conductive wires pass out under a rigid plastic connector sealed to the proximal end of the stethoscope. In another embodiment, a thermistor is situated inside the distal end adjacent the thin, flexible cuff, and the conductive wires are attached to a pair of end terminals mounted in the rigid plastic connector at the proximal end of the stethoscope.

The prior esophageal stethoscope have not been entirely satisfactory and possess a number of disadvantages and problems. When provided with a rigid plastic connector sealed or rigidly attached to the proximal end, it has been difficult to alter the length of the stethoscope. This places a restraint upon the physician and he must use stethoscope of fixed, predetermined length. When a temperature-sensing element forms an integral part of the stethoscope, altering the length of the stethoscope is substantially impossible.

When the type of temperature-sensing element differs from stethoscope to stethoscope, it is necessary for the hospital to maintain and have available the appropriate temperature-measuring instrument which, of necessity, must be calibrated with each different sensing element if accurate measurements are to be made. This problem is compounded since the esophageal stethoscope with its integral temperature-sensing element and electrical connections must be discarded after use and cannot be reused.

The present invention overcomes these serious problems by providing a universal measuring attachment for use with different sizes and types of esophageal stethoscopes and which may be sterilized and reused over an extended period of time. In addition, the measuring attachment is provided with an adjustably-positionable sensing probe which may be placed at any desired location within the stethoscope.

The sensing probe may be inserted into or withdrawn from the stethoscope, even during an operation, without disturbing the intubated stethoscope, thereby minimizing trauma to the patient. The invention not only reduces hospital costs by eliminating waste resulting from disposal but provides increased reliability and accuracy of measurements by employing reusable higher quality component parts, minimizing the need for recalibration.

BRIEF DESCRIPTION OF THE DRAWINGS

FIG. 1 is a side view of the preferred embodiment of the coupling adapter of the invention.

FIG. 2 is an end view of the preferred embodiment of FIG. 1.

FIG. 3 is a side view of an alternative embodiment of the invention.

FIG. 4 is an end view of FIG. 3.

FIG. 5 is a side view of another alternative embodiment of the invention.

FIG. 6 is an end view of FIG. 5.

FIG. 7 is a side view of still another embodiment of the invention.

FIG. 8 is a perspective view of the measuring attachment of the invention used with an esophageal stethoscope for monitoring the heart and respiration sounds and for measuring the temperature of a patient.

DESCRIPTION OF THE INVENTION

Referring to FIG. 1, coupling adapter 11, composed of a body of suitable resilient material, is provided with an input opening 12, an output opening 13, and a central bore 14 of uniform diameter extending completely through adapter 11 between openings 12 and 13. The body of adapter 11 is cylindrical in shape and may be composed of natural rubber; synthetic rubber, such as polyisoprene or neoprene; or other suitable polymer material, including polyvinyl chloride.

Adapter 11 is provided with a first tapered cylindrical section 15, adjacent input opening 12 and surrounding a portion of bore 14, for insertion into the open proximal end of a flexible esophageal stethoscope. A second tapered cylindrical section 16 of larger diameter than the first cylindrical section 15 surrounds bore 14 and is situated between section 15 and central body portion 17. Second cylindrical section 16 is adapted for insertion into the open proximal end of an esophageal stethoscope of larger size than first section 15. For example, tapered section 15 may be dimensioned for insertion into the flexible opening of a size 18 French stethoscope while section 16 may be dimensioned for use with a size 24 French stethoscope.

A shoulder 18, shown separating the first cylindrical section 15 from second cylindrical section 16, provides an abutment for the proximal end surface of the smaller esophageal stethoscope. Similarly, shoulder 19, between cylindrical section 16 and the central body portion 17, provides a stop for the proximal end surface of the larger stethoscope. While the preferred embodiment of FIG. 1 provides two tapered cylindrical sections 15 and 16 separated by shoulder 18 to accommodate two different sizes of stethoscopes, it is apparent that sections 15 and 16 may be combined into one long tapered section of varying diameter, and without a shoulder, to accommodate a variety of sizes of stethoscopes.

A cylindrical section 20, adjacent output opening 13 and surrounding a portion of bore 14, is provided for insertion into the conventional, flexible rubber tubing of the physician's earpiece or for coupling to an acoustically-responsive instrument. The patient's body sounds, such as heart beat and respiration, detected by an intubated stethoscope in the esophageal region, are conveyed through opening 12, central bore 14, and out through opening 13 into the flexible tubing.

Adapter 11 is provided with a laterally-extending body portion 21 extending outwardly from central portion 17 and terminating at end surface 22. A small passageway 23 extends through the center of laterally-extending body portion 21 from the end surface 22 into the central bore 14. Passageway 23 is provided for slidably passing a pair of insulated, conductive wires from the outside surface 22, through the passageway into central bore 14, and out through input opening 12. The first end terminals of the pair of conductive wires are electrically connected to an adjustably-positionable sensing probe, as described below in connection with FIG. 8.

The material used to form adapter 11 is selected to have a resilience sufficient to enable the side walls of passageway 23 to produce a firm but slidable grip upon the surface of the pair of insulated wires. The cross-sectional shape of passageway 23 is not limited to any particular geometric configuration, but a non-circular or oval shape is preferred. By virtue of the resilience of the material forming adapter 11, it is possible to alter the cross-sectional shape of passageway 23 from oval to circular by applying a compressional force on opposite sides of the laterally-extending portion 21. This feature enables the physician to release the firm grip upon the pair of insulated wires produced by the side walls of passageway 23 by squeezing the sides of laterally-extending portion 21 between the thumb and forefinger. Releasing the grip upon the wires permits the pair of insulated wires to easily slide through passageway 23.

FIG. 2 illustrates adapter 11 viewed from input opening 12. Oval passageway 23 extends from end surface 22 into the central bore 14, as shown. The width of laterally-extending body portion 21 is shown as being equal to the diameter of central body portion 17. Passageway 23 is illustrated as being wider in FIG. 2 than in FIG. 1 to represent its oval or non-circular cross-sectional shape.

The alternative embodiment of the invention of FIG. 3 shows coupling adapter 31 with an input opening 12, an output opening 13, and a central bore 14 extending between these two openings. First and second tapered, cylindrical sections 15 and 16 surround bore 14 at the input opening, and cylindrical section 20 surrounds bore 14 at the output opening 13. Adapter 31 is provided with shoulders 18 and 19, as in FIG. 1. Body portion 21 extends laterally outward from the central portion, terminating at end surface 22.

The laterally-extending passageway 33 of adapter 31 differs from that of adapter 11 of FIG. 1 by extending from the outside surface 22 through body portion 21 and the upper portions of tapered sections 15 and 16 without entry into central bore 14. Passageway 33 emerges from the end of tapered section 15 at opening 34.

The dimension and across-sectional shape of lateral passageway 33 is selected to permit easy sliding of the pair of conductive wires through the passageway. A firm grip upon the conductive wires is produced by the manual insertion of the first tapered cylindrical section 15 into the open end of the flexible esophageal stethoscope. The resilience of the material forming the first and second tapered cylindrical sections 15 and 16 and surrounding passageway 33 allows the compressional forces produced by the insertion of section 15 into the stethoscope to alter the shape of passageway 33. Compressing passageway 33 through section 15, or through section 16, produces a clamping force upon the pair of conductive wires.

FIG. 4 illustrates the end of adapter 31 viewed from input opening 12. Lateral passageway 33 extends from end surface 22 through body portion 21, emerging at opening 34.

The embodiment of coupling adapter 41, illustrated in FIG. 5, is similar, in part, to adapters 11 and 31 of FIGS. 1-4. Adapter 41 is provided with an input opening 12, and output opening 13, and a central bore 14. First and second tapered cylindrical sections 15 and 16 are provided with shoulders 18 and 19.

Adapter 41 differs from coupling adapters 11 and 31 by providing a lateral passageway 43, extending from outside end surface 22 through body portion 21 and emerging at opening 44 in shoulder 19. A longitudinally-extending groove 45 is situated in the upper outer surface of first and second tapered cylindrical sections 15 and 16. Groove 45 extends from opening 44 in shoulder 19, approximately parallel to bore 14, to the tip of cylindrical section 15 adjacent input opening 12. A pair of insulated, conductive wires are adapted for slidably passing from outside surface 22 through passageway 43 and within groove 45 for entry into the open end of the esophageal stethoscope. Insertion of tapered section 15 or 16 into the open end of the stethoscope applies a firm grip upon the conductive wires in groove 45.

The end view of adapter 41, illustrated in FIG. 6, shows lateral passageway 43, extending from end surface 22 through body portion 21 and emerging at opening 44 in shoulder 19. The U-shaped groove 45 extends from just below opening 44 to the tip of tapered cylindrical section 15.

The embodiment of coupling adapter 51, illustrated in FIG. 7, has an input opening 12, an output opening 13, and a central bore having two different diameter sections 54 and 55 extending between the two openings. A lateral passageway 53 extends from outside surface 22 through body portion 21 into the smaller diameter section 54. The larger diameter section 55 adjacent input opening 12 is tapered, as shown, for receiving the proximal end portion of the esophageal stethoscope. Shoulder 56, formed at the junction of diameter sections 55 and 54, provides an abutment for the proximal end surface of the stethoscope. Passageway 53 may have an oval or non-circular cross-section, as discussed above in connection with FIGS. 1 and 2, and is adapted for slidably passing a pair of wires from outside surface 22 through body portion 21 into the open end of the stethoscope.

FIG. 8 is a perspective view illustrating the manner in which the preferred embodiment of the invention is used with an esophageal stethoscope for monitoring heart and respiration sounds and for measuring the temperature of patients in the region of the esophagus. Esophageal stethoscope 60 consists of a long, hollow plastic tube 61, open at its proximal end 62 and perforated adjacent its distal end portion 63 by a group of spaced, cylindrical holes 64. The distal end of hollow plastic tube 61 and the group of spaced, cylindrical holes 64 are contained within and hermetically sealed by a thin, flexible cuff 65 surrounding distal end portion 63. When stethoscope 60 is intubated into the patient, the thin, flexible cuff 65 vibrates with the movement of the walls of the esophagus in response to the sounds of the heart beat and respiration to cause changes in the air pressure within hollow tube 61.

The sounds of the heart beat and respiration, as well as other body sounds in the region of the esophagus, are conveyed from stethoscope 60 to the physician's earpiece or to an acoustically-responsive instrument by means of coupling adapter 11. Input opening 12 and the tapered cylindrical section 15 are insertable into the open end 62 of stethoscope 60 with the end surface of open end 62 abutting shoudler 18. The sounds pass through the central bore, output cylindrical section 20, and output opening 13 to the flexible rubber tubing 71. Cylindrical section 20 is insertable into the open end of flexible rubber tubing 71, and the sounds are conveyed to the physician's earpiece or to an acoustically-responsive instrument.

The proximal end of certain conventional esophageal stethoscopes may be provided with a rigid plastic end connector having an output cylindrical section similar to section 20 of adapter 11 for insertion directly into flexible rubber tubing 17. In using the coupling adapter 11 of this invention with this type of stethoscope, the rigid plastic end connector is removed, as by cutting, thereby exposing the open proximal end 62, as shown in FIG. 8.

Where the stethoscope required to be intubated is of a size too large to provide an airtight fit upon first cylindrical section 15, input opening 12 and cylindrical section 15 may be inserted further into the open end 62 of the stethoscope until end 62 fits over the second cylindrical section 16 and abuts shoulder 19.

The temperature of the patient may be measured simultaneously with the monitoring of the patient's body sounds by means of the adjustably-positionable sensing probe 80 situated within the distal end portion 63 of stethoscope 60. Sensing probe 80, which may be a thermistor, thermocouple, semi-conductor or other temperature-responsive element, is electrically connected to the first end terminals of the pair of electrically-conductive, insulated wires 81. Conductive wires 81 are adjustably slidable within stethoscope tube 61 and extend out through end 62, through input opening 12 and the lateral passageway (not shown) of adapter 11 to electrical connector 82. A suitable conventional temperature-measuring instrument, coupled to connector 82 and calibrated with the temperature-sensing probe 80, provides the desired measurement.

Each of the pair of electrically-conductive wires 81 is composed of solid copper wire with a high-temperature, bonded, enamel-like insulated coating to provide long service life. The pair of conductive wires are illustrated as being twisted together to increase their stiffness. This configuration assures ease in handling by the physician while providing a low-friction surface for sliding through the lateral passageway of adapter 11 and through the hollow tube 61 of stethoscope 60.

To assist the physician in placing sensing probe 80 at any desired position within stethoscope 60, the pair of conductive wires 81 are provided with regularly-spaced, graduated markings, as at 83 and 84, to indicate the depth of penetration of probe 80 into the stethoscope.

While FIG. 8 illustrated the preferred embodiment of the invention, it is apparent that the embodiment of the coupling adapters illustrated in FIGS. 3-7 may be used instead of coupling adapter 11 without departing from the invention. It is also apparent that the measuring attachment is not limited solely to the measurement of temperature. Other suitable sensing probes, such as, for example, pressure transducers, microphones, or even light sources, may be electrically connected to the first end terminals of the pair of conductive wires 81 for insertion into the stethoscope, when desired.

In using the invention as illustrated in FIG. 8, the physician may elect to install the universal measuring attachment in place within the esophageal stethoscope before intubation. In this case, he will select the desired stethoscope, alter its length if desired, calibrate the sensing probe with its companion measuring unit, determine the depth of penetration of the probe, slide the conductive wires through the lateral passageway of the adapter to obtain the desired depth of penetration, insert the probe through the open proximal end of the stethoscope, slide the probe with its connecting wires down through the stethoscope tube, and manually insert the tapered cylindrical section of the adapter into the open proximal end of the stethoscope achieving a tight fit. This assembly procedure may be accomplished while the selected stethoscope remains completely within its sterilized package with only the seal of the package adjacent the open proximal end having been broken. The entire assembly may then be removed from the package, the distal cuff lubricated if required, and the stethoscope intubated into the patient.

Alternatively, the physician may, if he so chooses, intubate the selected sterilized stethoscope into the patient first, and then insert the prepared universal measuring attachment with its sensing probe into the intubated stethoscope. The physician also may remove the sensing probe with its connecting wires and supporting adapter, when desired, without disturbance of the intubated stethoscope. Thus, a variety of measurements may be made, even during an operation, with a minimum of trauma to the patient. After completion of the operation, the universal measuring attachment may be re-sterilized and stored for future use.

The universal measuring attachment of the invention may be used with a variety of sizes and types of esophageal stethoscopes. While the stethoscope itself must be discarded after use, to comply with accepted medical practice, the measuring attachment is sterilizable and may be reused over an extended period of time. Not only does this minimize waste and reduce hospital costs, it also permits the economic use of the highest quality component parts for the invention. As an example, the sensing probe can be the highest quality thermistor available, thereby providing increased accuracy and repeatability of temperature measurement. After calibration with the temperature measuring instrument, the sensing probe may be used in different stethoscopes for a number of measurements without re-calibration and without loss of accuracy.

Since the sensing probe with its connecting wires may be removed from the stethoscope at will, even after intubation, a variety of types of measurements may be made with the invention without disturbance of the intubated stethoscope, thereby minimizing trauma to the patient. The flexibility afforded by the invention enables the physician to select the stethoscope best suited for the operation, alter its length as desired, and adjustably locate the sensing probe at the most suitable position of measurement.

An many changes can be made in the above-described apparatus and many different embodiments of this invention could be made without departing from the scope thereof, it is intended that all matter contained in the above description or shown in the accompanying drawings shall be interpreted as illustrative and not in a limiting sense.

What is claimed is:

1. A measuring attachment for use with an esophageal stethoscope having an open proximal end and a closed distal end, comprising in combination:

(a) a coupling adapter composed of a body of resilient polymer material having an outside wall surface and having an input and an output opening;

(b) a hollow cylindrical bore extending completely through the body of said resilient adapter between said input and said output openings for the passage of sound waves therethrough, the portion of said adapter adjacent said input opening and surrounding said hollow cylindrical bore being a first cylindrical section for coupling to, and removal from, the open end of an esophageal stethoscope of a first diameter size, the body of said coupling adapter adjacent said first cylindrical section and surrounding said hollow cylindrical bore being a second cylindrical section having a diameter larger than the diameter of the first cylindrical section, said second cylindrical section being adapted for insertion into and removal from the open end of an esophageal stethoscope of a second and larger diameter size, said output opening being adapted for coupling to an acoustically responsive instrument;

(c) a lateral passageway extending from the outside wall surface of said resilient coupling adapter and through the body of said adapter into said hollow cylindrical bore;

(d) a pair of electrically-conductive wires situated within and extending through said lateral passageway, a portion of said hollow cylindrical bore, and out through said input opening, said pair of conductive wires having first and second pairs of end terminals, each pair of said end terminals being remotely situated with respect to said coupling adapter;

(e) a temperature-sensing element coupled to said first pair of end terminals, said temperature-sensing element being positioned with respect to said resilient coupling adapter by manually sliding said pair of conductive wires through said lateral passageway, said temperature-sensing element and said first pair of end terminals being adapted for insertion into and removal from the open end of an esophageal stethoscope, said pair of electrically-conductive wires being of sufficient stiffness to permit the positioning and retention of said temperature-sensing element at any desired, selected position within the esophageal stethoscope, said temperature-sensing element being retained in its selected position within the esophageal stethoscope upon the coupling of the first or second cylindrical section of said resilient coupling adapter to the open end of the esophageal stethoscope; and (f) means attached to said second pair of end terminals for coupling the output from said temperature-sensing element to a remotely-located temperature-measuring instrument.

2. The measuring attachment as defined by claim 1 wherein the cross-sectional shape of said lateral passageway extending through the body of said coupling adapter may be altered by applying a compressional force upon the body of resilient polymer material surrounding said passageway.

3. The measuring attachment as defined by claim 2 wherein the cross-sectional shape of said lateral passageway is non-circular, and wherein a compressional force applied to the body of resilient polymer material surrounding said passageway alters the cross-sectional shape of said passageway to permit sliding of the pair of electrically-conductive wires situated therein.

4. A measuring attachment for use with an esophageal stethoscope having an open proximal end and a closed distal end, comprising in combination:

(a) a coupling adapter composed of a body of resilient polymer material having an outside surface and having an input and an output opening;

(b) a hollow cylindrical bore extending completely through said resilient adapter between said input and said output openings for the passage of sound, the portion of said adapter adjacent said input opening and surrounding said hollow cylindrical bore being a first cylindrical surface for coupling to, and removal from, the open end of an esophageal stethoscope, said output opening being adapted for coupling to an acoustically-responsive instrument;

(c) a lateral passageway extending from the outside surface of said resilient coupling adapter and through said adapter for entry into said hollow cylindrical bore;

(d) a pair of electrically-conductive wires situated within and extending through said lateral passageway into said hollow cylindrical bore and out through said input opening, said pair of conductive wires having a first pair of end terminals remotely situated with respect to said lateral passageway; and (e) a sensing probe coupled to said first pair of end terminals, said sensing probe being adapted for adjustable-positioning within the esophageal stethoscope at any desired, selected position therein by slidably positioning said pair of conductive wires within said lateral passageway, the resilient walls of said lateral passageway slidably passing and gripping said pair of conductive wires, said pair of electrically-conductive wires being provided with sufficient stiffness to assure retention of said sensing probe at the desired, selected position within the esophageal stethoscope, said pair of conductive wires having a second pair of end terminals remotely situated with respect to said lateral passageway for connecting to an external measuring instrument.

5. A measuring attachment for use with an esophageal stethoscope having an open proximal end and a closed distal end, comprising in combination:

(a) a coupling adapter composed of a cylindrical body of resilient polymer material having an outside surface and having an input and an output opening;

(b) a hollow cylindrical bore extending completely through said resilient adapter between said input and said output openings for the passage of sound waves, the section of said cylindrical body adjacent said input opening and surrounding said bore being tapered for coupling to, and removal from, the open end of an esophageal stethoscope, said output opening being adapted for coupling to an acoustically-responsive instrument;

(c) a lateral passageway extending from the outside surface of said resilient coupling adapter and through the resilient body of said adapter into said hollow cylindrical bore;

(d) a pair of relatively stiff electrically-conductive wires situated within and extending through said lateral passageway, a portion of said bore, and out through said input opening; said pair of conductive wires having first end terminals remotely situated with respect to said coupling adapter;

(e) a sensing element coupled to said first end terminals, said sensing element being positioned with respect to said resilient coupling adapter by sliding said pair of conductive wires through said lateral passageway, the walls of said lateral passageway slidably passing and gripping said pair of conductive wires, said sensing element coupled to said first end terminal of said electrically-conductive wires being insertable into and removable from the esophageal stethoscope without disturbance of the esophageal stethoscope, said sensing element being retained at its selected depth of penetration within the esophageal stethoscope by insertion of the tapered input section of said adapter into the open proximal end of the esophageal stethoscope, said pair of conductive wires having second end terminals remotely situated with respect to said coupling adapter; and (f) connector means coupled to said second end terminals, said connector means being adapted for connecting the output from said sensing element to a remotely-located measuring instrument.

6. A measuring attachment for use with an esophageal stethoscope having an open proximal end and a closed distal end, comprising in combination:

(a) a coupling adapter composed of a cylindrical body of polymer material having an outside surface and having an input and an output opening;

(b) a hollow cylindrical bore extending through said cylindrical adapter between said input and output openings, the portion of said cylindrical adapter adjacent said input opening and surrounding said hollow cylincrical bore being adapted for coupling to the open proximal end of an esophageal stethoscope;

(c) a cylindrically shaped passageway extending from the outside surface of said cylindrical adapter and through the body of said cylindrical adapter into said hollow cylindrical bore, said cylindrically shaped passageway being laterally displaced with respect to said hollow cylindrically shaped bore;

(d) a pair of electrically conductive wires having a first and a second pair of end terminals and an intermediate portion located between said first and second pair of end terminals, said intermediate portion extending from the outside surface of said cylindrical adapter into a portion of said hollow cylindrical bore and out through said input opening, said first and second pairs of end terminals being remotely situated with respect to said cylindrical adapter; and (e) an electrically responsive probe coupled to said first pair of end terminals, said probe being adapted for adjustable positioning within the esophageal stethoscope at any desired position therein upon insertion into the esophageal stethoscope through its open proximal end, said intermediate portion of said pair of electrically conductive wires being slideably positionable with respect to said cylindrical adapter, said cylindrical adapter including resilient polymer means surrounding said intermediate portion for slideably passing and gripping said pair of electrically conductive wires, said pair of electrically conductive wires being provided with sufficient stiffness to assure retention of said probe at the desired, selected position within the esophageal stethoscope when the portion of said cylindrical adapter adjacent said input opening is coupled to the open proximal end of the esophageal stethoscope, said second pair of end terminals remotely situated with respect to said cylindrical adapter being adapted for connecting to an external, remotely located instrument.

* * * * *